(12) United States Patent
Williams

(10) Patent No.: US 8,396,568 B2
(45) Date of Patent: *Mar. 12, 2013

(54) MEDICAL ELECTRICAL LEAD BODY DESIGNS INCORPORATING ENERGY DISSIPATING SHUNT

(75) Inventor: Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1054 days.

This patent is subject to a terminal disclaimer.

(21) Appl. No.: 11/741,568

(22) Filed: Apr. 27, 2007

(65) Prior Publication Data

US 2007/0208383 A1 Sep. 6, 2007

Related U.S. Application Data

(63) Continuation-in-part of application No. 10/909,518, filed on Aug. 2, 2004, now Pat. No. 7,783,365, which is a continuation-in-part of application No. 10/407,653, filed on Apr. 4, 2003.

(60) Provisional application No. 60/371,995, filed on Apr. 11, 2002.

(51) Int. Cl.
*A61N 1/00* (2006.01)

(52) U.S. Cl. ........................................... 607/122
(58) Field of Classification Search .................. 607/122, 607/116, 63
See application file for complete search history.

(56) References Cited

U.S. PATENT DOCUMENTS

| | | | |
|---|---|---|---|
| 4,161,952 A | 7/1979 | Kinney | |
| 4,602,637 A | 7/1986 | Elmqvist et al. | |
| 4,840,186 A | 6/1989 | Lekholm et al. | |
| 4,934,049 A | 6/1990 | Kiekhafer et al. | |
| 5,042,143 A * | 8/1991 | Holleman et al. | 29/825 |
| 5,201,903 A * | 4/1993 | Corbett et al. | 29/872 |
| 5,292,338 A | 3/1994 | Bardy | |
| 5,347,708 A * | 9/1994 | Bischoff et al. | 29/825 |
| 5,358,516 A | 10/1994 | Myers et al. | |
| 5,366,496 A | 11/1994 | Dahl et al. | |
| 5,411,544 A * | 5/1995 | Mar et al. | 607/122 |
| 5,439,485 A * | 8/1995 | Mar et al. | 607/119 |
| 5,445,859 A | 8/1995 | Lindegren et al. | |
| 5,466,252 A | 11/1995 | Soukup et al. | |
| 5,466,253 A | 11/1995 | Doan | |
| 5,542,173 A * | 8/1996 | Mar et al. | 29/825 |
| 5,628,774 A * | 5/1997 | Helland et al. | 607/116 |
| 5,674,272 A | 10/1997 | Bush et al. | |
| 5,845,396 A | 12/1998 | Altman et al. | |
| 5,849,031 A | 12/1998 | Martinez et al. | |
| 5,871,530 A * | 2/1999 | Williams et al. | 607/122 |
| 5,876,431 A | 3/1999 | Spehr et al. | |

(Continued)

FOREIGN PATENT DOCUMENTS

| | | |
|---|---|---|
| EP | 0 622 089 A2 | 2/1994 |
| WO | WO0232500 A | 4/2002 |

(Continued)

OTHER PUBLICATIONS

International Search Report, PCT/US2008/052574, Mar. 7, 2008, 5 Pages.

*Primary Examiner* — Eric D Bertram
*Assistant Examiner* — Roland Dinga
(74) *Attorney, Agent, or Firm* — Stephen W. Bauer; Michael J. Ostrom

(57) ABSTRACT

An elongate body of a medical electrical lead includes at least one conductor formed into a coil that includes a first portion and a second portion, wherein the first portion extends within an outer insulation sheath and the second portion extends outside the outer insulation sheath to be exposed to an environment external to the lead body as an energy dissipating shunt.

13 Claims, 3 Drawing Sheets

U.S. PATENT DOCUMENTS

| | | | |
|---|---|---|---|
| 5,957,965 A * | 9/1999 | Moumane et al. | 607/117 |
| 5,957,970 A | 9/1999 | Shoberg et al. | |
| 6,029,089 A * | 2/2000 | Hawkins et al. | 607/37 |
| 6,104,960 A * | 8/2000 | Duysens et al. | 607/117 |
| 6,216,045 B1 | 4/2001 | Black et al. | |
| 6,289,250 B1 | 9/2001 | Tsuboi et al. | |
| 6,374,141 B1 | 4/2002 | Sass | |
| 6,501,992 B1 * | 12/2002 | Belden et al. | 607/122 |
| 6,615,695 B1 | 9/2003 | Hjelle et al. | |
| 6,673,999 B1 * | 1/2004 | Wang et al. | 174/36 |
| 6,980,865 B1 | 12/2005 | Wang et al. | |
| 6,981,314 B2 | 1/2006 | Black et al. | |
| 7,010,358 B1 | 3/2006 | Kroll et al. | |
| 7,047,627 B2 | 5/2006 | Black et al. | |
| 7,174,220 B1 | 2/2007 | Chitre et al. | |
| 7,277,762 B2 | 10/2007 | Boser | |
| 7,627,382 B2 | 12/2009 | Minar et al. | |
| 7,917,213 B2 | 3/2011 | Bulkes et al. | |
| 2003/0045920 A1 * | 3/2003 | Belden et al. | 607/122 |
| 2003/0069521 A1 * | 4/2003 | Reynolds et al. | 600/585 |
| 2003/0092303 A1 * | 5/2003 | Osypka | 439/274 |
| 2003/0144718 A1 | 7/2003 | Zeijlemaker | |
| 2004/0263172 A1 | 12/2004 | Gray et al. | |
| 2005/0159801 A1 | 7/2005 | Marshall et al. | |
| 2006/0009819 A1 | 1/2006 | Przbyszewski | |
| 2006/0200218 A1 | 9/2006 | Wahlstrand | |
| 2008/0009905 A1 | 1/2008 | Zeijlemaker | |
| 2009/0149920 A1 | 6/2009 | Li et al. | |
| 2010/0016936 A1 * | 1/2010 | Stevenson et al. | 607/116 |

FOREIGN PATENT DOCUMENTS

| | | |
|---|---|---|
| WO | WO03063954 A | 8/2003 |
| WO | WO2006017421 A | 2/2006 |

* cited by examiner

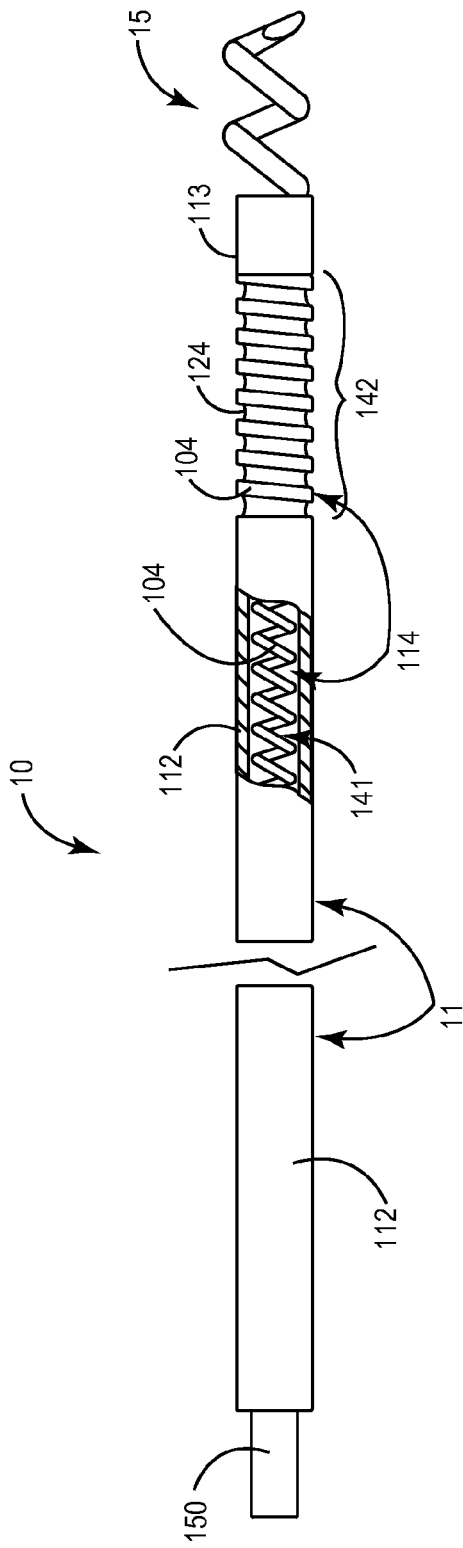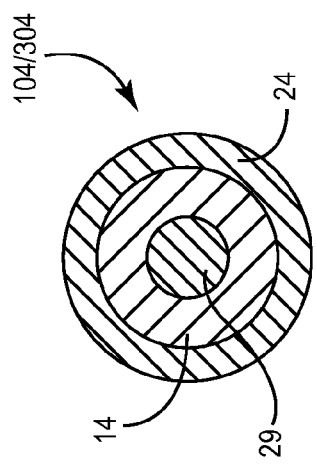

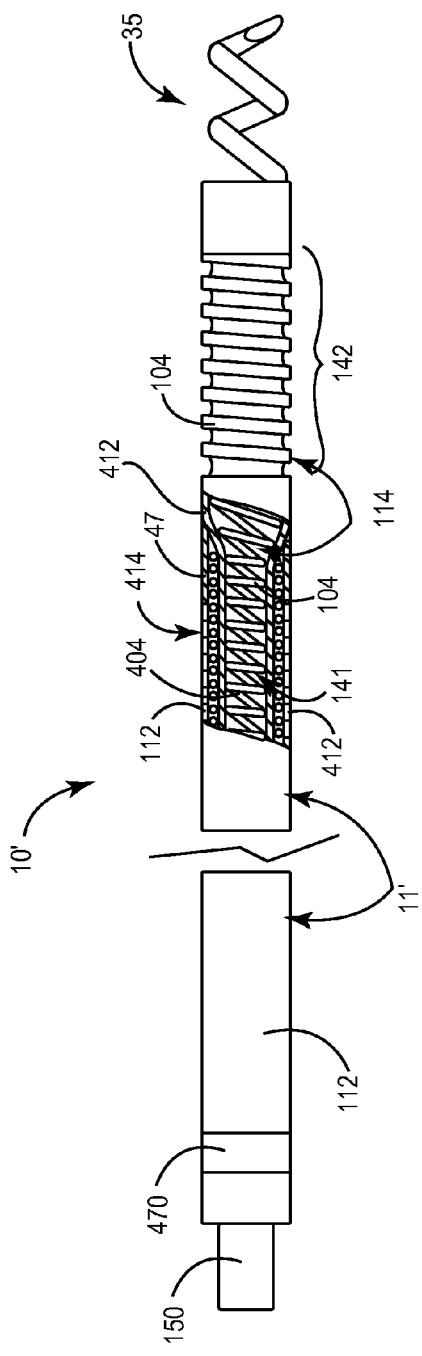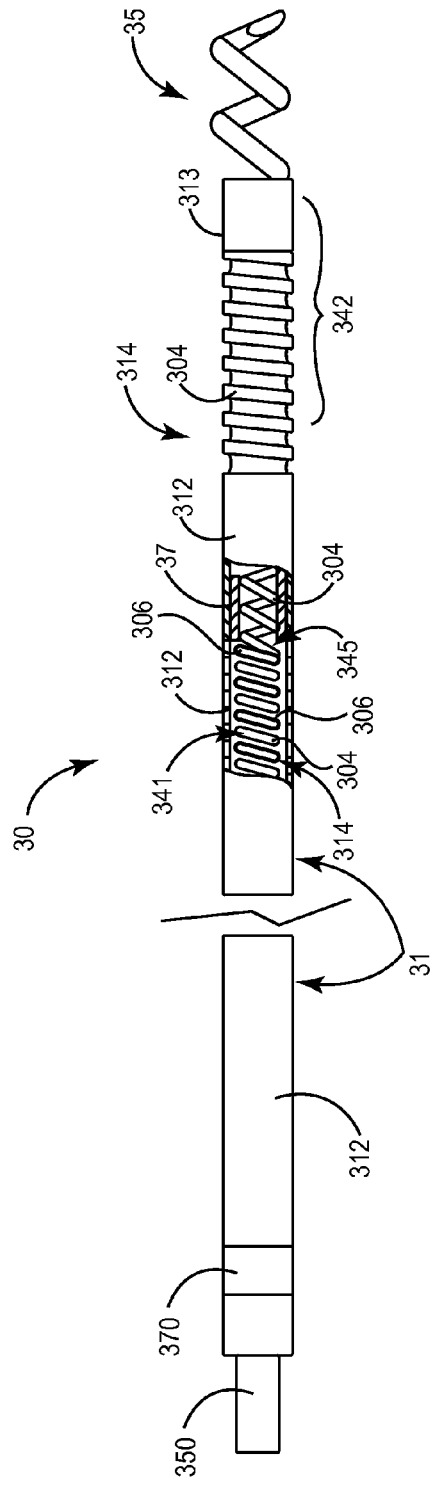

US 8,396,568 B2

MEDICAL ELECTRICAL LEAD BODY DESIGNS INCORPORATING ENERGY DISSIPATING SHUNT

CROSS REFERENCE TO RELATED APPLICATION

The present invention is a continuation-in-part of U.S. application Ser. No. 10/909,518, filed Aug. 2, 2004, now U.S. Pat. No. 7,783,365 now published as 20050004643, entitled "Implantable medical device conductor insulation and process for forming," which is a continuation-in-part of U.S. application Ser. No. 10/407,653, filed Apr. 4, 2003, now published as 20030216800, entitled "Implantable medical device conductor insulation and process for forming," which is a utility application filed off of U.S. Provisional Application Ser. No. 60/371,995, filed Apr. 11, 2002.

TECHNICAL FIELD

The present invention pertains to medical electrical leads and more particularly to medical electrical leads including energy dissipating shunts.

BACKGROUND

The technology explosion in the medical device industry has resulted in a variety of innovative diagnostic and therapeutic devices and methods. Many implantable medical devices (IMDs), for example, including pacemakers, cardioverter-defibrillators and neural stimulators, are operatively coupled to electrodes, which are joined to elongate lead wires that extend from the devices to a target site either on or within a body of a patient. The electrodes may deliver stimulation therapy and/or sense electrical signals from the patient, for example cardiac depolarization signals, which are used to guide or dictate therapy delivery.

Patients, in which such leads are implanted, may be exposed to a substantial amount of radio frequency (RF) energy, for example, when subject to magnetic resonance imaging (MRI) or radio diathermy processes. An implanted lead wire can act as an antenna during exposure to these RF signals and an appreciable amount of current may thereby be generated in the lead wire, resulting in high current concentration at a surface of a tissue-contacting electrode, for example, implanted to provide pacing stimulation. Much of this current produces heat, due to energy dissipated in a resistance of the electrode-to-tissue interface, which may result in tissue damage in proximity to the electrode. Leads that include an energy dissipating shunt component have been described, for example, in co-pending and commonly-assigned patent application Ser. No. 11/426,207, but there is still a need for novel lead body designs that incorporate more effective energy dissipating shunts.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1 is a plan view including a partial section view of a medical electrical lead.

FIG. 2 is a cross-section view through a conductor of FIG. 1.

FIG. 3 is a plan view including a partial section view of a coaxially constructed medical electrical lead.

FIG. 4 is a plan view including a partial section view of a multi-conductor medical electrical lead.

DETAILED DESCRIPTION

Figure 5:
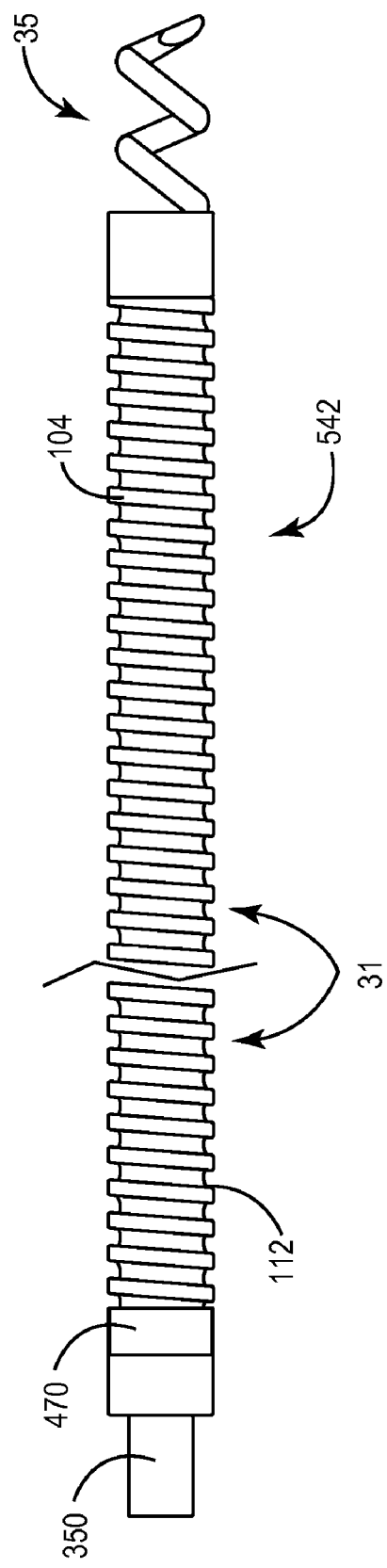
FIG. 5 is a plan view including a partial section view of a coaxially constructed medical electrical lead.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

FIG. 1 is a plan view including a partial section view of a medical electrical lead 10, according to some embodiments of the present invention. FIG. 1 illustrates lead 10 including an elongate lead body 11 terminated at a proximal end by a connector pin 150 and terminated at a distal end by a stimulation electrode 15. Those skilled in the art will understand that connector pin 150 may be coupled to an implantable pulse generator, for example, a pacemaker device, and that electrode 15 may act as both a sensing and stimulation electrode when coupled to myocardial tissue. According to the illustrated embodiment, electrode 15 is coupled to connector pin 150 by a conductor 104 formed into a coil 114; coil 114 includes a first portion 141, which extends within an outer insulation sheath 112, and a second portion 142 (also referred to as a shunt), which extends outside sheath 112, to form an energy dissipating shunt when lead 10 picks up radio frequency (RF) energy, for example, during an magnetic resonance imaging (MRI) procedure. According to an alternate embodiment, coil 114 includes more than one conductor 104, being what is known in the art as a multi-filar coil, and the multiple filars or conductors 104 may extend along an entire length of coil 114 between connector pin 150 and electrode 15. FIG. 1 further illustrates another outer insulation sheath 113 extending over coil 114 between second portion, or shunt 142 and electrode 15. Insulation sheaths 112, 113 are formed from insulative material. Exemplary insulative materials include silicone, polyurethane, a combination thereof etc.

FIG. 2 is a cross-section view through conductor 104. FIG. 2 illustrates conductor 104 including a wire 14 having an outer jacket of insulation 24 (or insulative layer) extending about an entire circumference thereof. Wire 14 may have an outer diameter in a range from about 0.003 inch to about 0.006 inch. Outer jacket of insulation 24 extends at least along a length of conductor 104 that forms second portion or shunt 142. According to embodiments of the present invention, insulation 24 provides a high enough impedance, between wire 14 and an implant environment of lead 10, so that relatively low frequency stimulation pulses may pass through conductor 104 to electrode 15 without current leakage along shunt 142, and provides for a capacitive coupling with the environment external to lead 10 for the current induced by relatively high frequency RF energy, which may be picked up by conductor 104, so that a high current concentration at the relatively small tissue-contacting surface of electrode 15 is prevented. It should be noted that a length of shunt 142, and a position of shunt 142, when lead 10 is implanted, are such that the energy of the relatively high-frequency current will be dissipated over a relatively large surface area, resulting in a reduced local energy density and, thus, a reduced temperature rise, thereby avoiding tissue damage. Insulation 24 may be any dielectric, biostable and biocompatible material, for example an oxide, a polymer, or a ceramic, but is preferably one that can sustain repeated flexing imposed by a cardiac implant environment, either endocardial or epicardial, without sustaining breaches. Insulation jacket 24 may have a thickness in a range from about 0.0001 inch to about 0.001 inch.

According to some embodiments of the present invention, jacket 24 extends along an entire length of conductor 104 to form a primary insulation for sensing and stimulation between connector pin 150 to electrode 15; according to some alternate embodiments, jacket 24 only extends along a length of conductor 104, which forms second portion 142 of coil 114, to act as a primary insulation for only second portion 142, while outer insulation sheaths 112, 113 act as a primary insulation for first portion 141 of coil and that portion extending between second portion 142 and electrode 15, respectively. According to preferred embodiments of the present invention, conductor 104 includes a single conductor wire, for example, wire 14, which is continuous from a junction with connector pin 150 to a junction with electrode 15. A length of second portion 142 may be between about 3 centimeters and about 7 centimeters, or even approaching an entire length of lead 10, for example, between about 30 centimeters and about 110 centimeters; and a length of second insulation sheath 113, providing a spacing between second portion 142 and electrode 15, is greater than about 3 millimeters, and, preferably, less than about 6 to 8 centimeters.

FIG. 2 further illustrates wire 14 including an optional 'low-resistance' core 29, for example, formed from silver, tantalum or gold, to decrease a resistance of wire 14. Such a decrease may be desirable in order to increase a number of turns of coil 114, thereby increasing an inductance of conductor 104 without significantly increasing a resistance thereof. Careful selection of increased inductance (e.g. increased number of turns in a coil, etc.) of conductor coil 104 reduces the current induced by the MRI. By increasing the inductive impedance, minimal (i.e. less than a half degree on the tip) or no energy is delivered to the tip of the electrode by increasing the high-frequency (i.e. 21 megaHertz (Mhz) to 128 MHz) impedance of conductor 104 to electrode 15. With reference back to FIG. 1, according to a preferred embodiment, an outer diameter of coil 114 is increased along second portion 142 in order to be about flush with an outer diameter of adjacent insulation sheaths 112 and 113. FIG. 1 further illustrates a filler material 124, for example, formed by silicone rubber, between turns of second portion 142 of coil 114, which may lend some mechanical stability to portion 142 and may prevent tissue in-growth between the turns. Silicone rubber is commercially available from Silicone Specialties Fabricators located in Elk Rapids, Mich. According to some alternate embodiments, coil 114, either just along second portion 142, or along an entire length thereof, may be mounted on a flexible insulative core, which may or may not include a longitudinally extending lumen. Embodiments including such a core may also include filler material 124 along second portion 142. According to yet further alternate embodiments, first portion 141 of coil 114 may be embedded in sheath 112.

According to an exemplary embodiment of the present invention, coil 114 of lead 10 is bi-filar, including two of conductors 104 wound coaxially side-by-side; and key dimensions for lead 10 are as follows: an overall length of lead 10 is about 68 cm; wire 14, preferably formed from silver-cored MP35N alloy, has a diameter of about 0.003 inch; insulation jacket 24, preferably formed from one of polytetrafluoroethylene (PTFE), tetrafluorethylene hexafluoropropylene vinylidene fluoride (THV), a fluorinated terpolymer, ethylene tetrafluoroethylene (ETFE), polyvinylidene fluoride (PVD) THV 400, THV 600, and Si polyimide. Insulation jacket 24 has a thickness of about 0.0005 inch; insulation sheath 112, preferably formed from polyurethane, has an outer diameter of about 0.055 inch; second portion 142 of coil 114 has an outer diameter of about 0.055 inch and a length of about 6 cm; a pitch of coil 114, at least along second portion 142 is about 0.012 inch; and insulation sheath 113, preferably formed from polyurethane, has a length of about 1.5 cm. With respect to the Si polyimide, it is preferable to use hydrolytically stable polyimide. According to this exemplary embodiment, a capacitance of shunt 142 is between about 400 and 500 picoFarads. It should be noted that the Si polyimide insulative jacket may be as thin as about 0.0002 inch to further increase the capacitance. Alternate constructions of leads including shunts that are integral along a length of an electrode conductor thereof, similar in nature to shunt 142, will be described below.

FIG. 3 is a plan view including a partial section view of a coaxially constructed medical electrical lead 10', according to some embodiments of the present invention. FIG. 3 illustrates lead 10' including conductor coil 114 coupling connector pin 150 to electrode 15, as previously described for lead 10, wherein coil 114 includes first portion 141 extending within outer insulation sheath 112 and second portion, or shunt 142 extending outside sheath 112. According to the illustrated embodiment, a lead body 11' of lead 10' further includes another conductor 404 formed into a coil 414 extending about coaxially about coil 114 and isolated therefrom by an inner insulation sheath 412, for example formed from silicone or polyurethane; conductor 404 couples another electrode 47, which is disposed proximal to shunt 142, to a connector ring 470, which is disposed in proximity to connector pin 150. Those skilled in the art will appreciate that electrode 47 in conjunction with electrode 15 may form a bipolar pair for sensing and stimulation, however, it should be noted that electrodes 47 and 15 may function independently of one another. According to the illustrated embodiment, inner insulation sheath 412 extends distal of electrode 47 where an outer diameter thereof is increased to be about flush with an outer diameter of electrode 47; an outer diameter of shunt 142 is preferably about flush with the outer diameter of sheath 412 distal to electrode 47, which may be about equal to an outer diameter of sheath 112. Although FIG. 3 illustrates a ring component forming electrode 47, it should be understood that such a component is not necessary and an exposed portion of coil 414, distal to sheath 112, may form electrode 47.

FIG. 4 is a plan view including a partial section view of a multi-conductor medical electrical lead 30, according to some embodiments of the present invention. FIG. 4 illustrates lead 30 including an elongate lead body 31 terminated at a proximal end by a connector pin 350 and terminated at a distal end by a first electrode 35; lead 30 further includes a second electrode 37 disposed proximal to first electrode 35 and a connector ring 370 disposed in proximity to pin 350. According to the illustrated embodiment, first electrode 35 is coupled to pin 350 by a first conductor 304 formed into a coil 314, and second electrode 37 is coupled to ring 370 by a second conductor 306 also formed into coil 314. FIG. 4 further illustrates coil 314 including a first portion 341, which extends within an outer insulation sheath 312, a second portion 342, which extends outside sheath 312 to form an energy dissipating shunt when lead 30 picks up RF energy, and another outer insulation sheath 313 extending over coil 314 between second portion, or shunt 342 and electrode 35. Second conductor 306 is shown terminated in proximity to a distal end 345 of coil first portion 341 to join with electrode 37, and first conductor 304 is shown extending within a bore of electrode 37, past distal end 345 of first coil portion 341, to second coil portion, or shunt 342. Like shunt 142 (FIG. 1), shunt 342 is shown having an outer diameter about equal to an outer diameter of outer insulation sheath 312.

With reference back to FIG. 2, conductor 304 includes wire 14, which may include the illustrated low-resistance core 29, as previously described, and insulation jacket 24, which extends about an entire circumference thereof to electrically isolate conductor 304 from conductor 306, along first portion 341 of coil 314, and from the environment external to lead 30, along coil second portion, or shunt 342, during transmission of relatively low frequency stimulation pulses from connector pin 350 to electrode 35. According to alternate embodiments, second conductor 306 includes jacket of insulation 24 along first portion 341 of coil 314, and first conductor may only include jacket of insulation 24 along second portion 342 of coil 314. As previously described for conductor 104, insulative jacket 24 around wire 14 of first conductor 304 along shunt 342 provides capacitive coupling for the current induced by relatively high frequency RF energy, thereby preventing a high current density at the relatively small tissue-contacting surface of electrode 35; and a length and disposition of shunt 342 safely dissipates energy of the relatively high frequency current along shunt 342. According to preferred embodiments of the present invention, wire 14 of first conductor 304 is continuous from connector pin 350 to electrode 35.

FIG. 5 depicts medical electrical lead 542. Medical electrical lead 542 is similar to the medical electrical lead depicted in FIG. 4 except that lead 542 has an energy dissipating shunt 342 that extends a substantial length of lead 542. Lead 542 may extend from about 25 centimeter to about 110 centimeters. Specifically, medical electrical lead 542 includes an elongate lead body 31 terminated at a proximal end by a connector pin 350 and terminated at a distal end by a first electrode 35. Lead 31 further includes a second electrode 37 disposed proximal to first electrode 35 and a connector ring 370 disposed in proximity to pin 350. First electrode 35 is coupled to pin 350 by a first conductor 304 formed into a coil 314, and second electrode 37 is coupled to ring 370 by a second conductor 306 also formed into coil 314. Skilled artisans appreciate that for the sake of clearly depicting an elongated shunt 342, some of the elements described and shown relative to FIG. 4 are not repeated in FIG. 5. Additionally, while some of the leads herein are depicted in a coaxial configuration, a multi-conductor configuration may also be implemented with this embodiment.

In the foregoing detailed description, the invention has been described with reference to specific embodiments. However, it may be appreciated that various modifications and changes can be made without departing from the scope of the invention as set forth in the appended claims.

I claim:

1. A medical electrical lead, comprising:
a stimulation electrode located near a distal end of the lead;
a connector pin located near a proximal end of the lead; and
an energy dissipating shunt that, when implanted, is exposed to an environment external to the lead for a substantial length of the lead between the connector pin and the stimulation electrode;
the energy dissipating shunt being formed from a coiled conductor that includes a wire and an insulative layer extending about an entire circumference of the wire, the coiled conductor being exposed to the environment external to the lead for the substantial length of the lead to form the energy dissipating shunt,
the energy dissipating shunt being designed to provide a high enough impedance so that relatively low frequency stimulation pulses are transmitted through the wire and to provide capacitive coupling of current induced on the wire by high frequency RF energy to the environment external to the lead over the substantial length of the lead,
wherein a thickness of the insulative layer is between about 0.0001 inch and about 0.001 inch.

2. The lead of claim 1, wherein the insulative layer comprises a polymer.

3. The lead of claim 1, wherein a length of the lead is between about 30 centimeters and about 110 centimeters and the energy dissipating shunt is exposed to an environment external to the lead for a substantial length of the lead.

4. The lead of claim 1, wherein a distal end of the energy dissipating shunt is spaced apart from the stimulation electrode by a distance greater than about 3 millimeters.

5. The lead of claim 1, wherein a thickness of the insulative layer is about 0.0005 inches.

6. The lead of claim 1, wherein the coiled conductor forming the energy dissipating shunt includes a plurality of coils having a pitch of about 0.012 inches.

7. The lead of claim 1, wherein the energy dissipating shunt has a capacitance between about 400 and 500 picoFarads.

8. The lead of claim 1, wherein the insulative layer is formed from at least one of polytetrafluoroethylene (PTFE), tetrafluorethylene hexafluoropropylene vinylidene fluoride (THV), a fluorinated terpolymer, ethylene tetrafluorethylene (ETFE), polyvinylidene fluoride (PVD) THV 400, THV 600, and SI polyimide.

9. The lead of claim 1, wherein the plurality of coils have a pitch that results in space between adjacent turns, the lead further comprising a non-conductive filler material that fills at least the space between turns of the coiled conductor.

10. The lead of claim 9, wherein the filler material comprises a silicone rubber.

11. The medical electrical lead of claim 1, wherein the high frequency RF energy is RF energy between 21 megahertz (MHz) and 128 MHz.

12. The medical electrical lead of claim 1, wherein the high frequency RF energy is RF energy from a magnetic resonance imaging (MRI) or radio diathermy processes.

13. The medical electrical lead of claim 1, wherein the relatively low frequency stimulation pulses are pacing stimulation pulses.

* * * * *